US006667007B1

(12) United States Patent
Schmidt

(10) Patent No.: US 6,667,007 B1
(45) Date of Patent: *Dec. 23, 2003

(54) SYSTEM AND METHOD OF APPLYING ENERGETIC IONS FOR STERILIZATION

(75) Inventor: John A. Schmidt, Princeton, NJ (US)

(73) Assignee: The Trustees of Princeton University, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/164,838

(22) Filed: Jun. 7, 2002

Related U.S. Application Data

(63) Continuation-in-part of application No. 09/760,513, filed on Jan. 12, 2001, now Pat. No. 6,403,029.
(60) Provisional application No. 60/175,785, filed on Jan. 12, 2000.

(51) Int. Cl.⁷ .................................................. A61L 2/14
(52) U.S. Cl. ........................... 422/22; 422/23; 204/164; 315/111.81
(58) Field of Search ...................... 422/22, 23; 204/164; 315/111.81

(56) References Cited

U.S. PATENT DOCUMENTS

| | | | |
|---|---|---|---|
| 3,383,163 A | 5/1968 | Menashi | 21/54 |
| 5,089,747 A | 2/1992 | Koshiishi et al. | 315/111.81 |
| 5,393,490 A | 2/1995 | Jacob | 422/22 |
| 5,603,893 A | 2/1997 | Gundersen et al. | 422/22 |
| 5,607,509 A * | 3/1997 | Schumacher et al. | 118/723 FE |
| 6,078,490 A * | 6/2000 | Walters | 361/88 |
| 6,403,029 B1 * | 6/2002 | Schmidt | 422/22 |

OTHER PUBLICATIONS

Russell, "The Destruction of Bacterial Spores," Academic Press, 1982, pp. 110–123.
Tanaka, et al., "Dimondlike Carbon Deposition on Plastic Films by Plasma Source Ion Implantation," J. Vac. Sci. Technol. A 20(3), May/Jun. 2002, pp. 625–633.
Meixler, L. and J. Schmidt, "Surface Sterilization with High Energy Ions," Abstract, International Conference on Plasma Science, IEEE Nuclear and Plasma Sciences Society, Banff, Canada, May 26–30, 2002 (1 page).
Meixler, L. and J. Schmidt, "Surface Sterilization with High Energy Ions", Slide Presentation, May 29, 2002, International Conference on Plasma Science, IEEE Nuclear and Plasma Sciences Society, Banff, Canada, May 26–30, 2002 (16 pages).

* cited by examiner

*Primary Examiner*—Robert J. Warden, Sr.
*Assistant Examiner*—Sean E. Conley
(74) *Attorney, Agent, or Firm*—Wolff & Samson PC

(57) ABSTRACT

A method of sterilization of a container is provided whereby a cold plasma is caused to be disposed near a surface to be sterilized, and the cold plasma is then subjected to a pulsed voltage differential for producing energized ions in the plasma. Those energized ions then operate to achieve spore destruction on the surface to be sterilized. Further, a system for sterilization of a container which includes a conductive or non-conductive container, a cold plasma in proximity to the container, and a high voltage source for delivering a pulsed voltage differential between an electrode and the container and across the cold plasma, is provided.

17 Claims, 1 Drawing Sheet

SYSTEM AND METHOD OF APPLYING ENERGETIC IONS FOR STERILIZATION

RELATED APPLICATIONS

The present invention is a continuation-in-part application of U.S. patent application Ser. No. 09/760,513 filed Jan. 12, 2001, now U.S. Pat. No. 6,403,029, issued Jun. 11, 2002, which is related to and claims the benefit of U.S. Provisional Patent Application Ser. No. 60/175,785, filed Jan. 12, 2000, both applications of which are assigned to the same assignee and incorporated herein by reference.

STATEMENT OF GOVERNMENT INTERESTS

This invention was made with government support under U.S. Department of Energy Grant No. DE-FG03-98DP00210. The government has certain rights in this invention.

FIELD OF THE INVENTION

The invention relates to sterilization processing and particularly to the use of energetic ions for the sterilization of surfaces.

BACKGROUND OF THE INVENTION

In the field of food processing, as well as in other fields, sterilization to protect against danger from harmful microorganisms is a critical concern. For the food industry, the sterilization of containers for food products is particularly important, and improvements in container sterilization processes can be expected to have a large economic impact. In the current art, sterilization of an object may be carried out by subjecting the object to heated steam pressure, to permeation by a gas such as hydrogen peroxide or ethylene oxide, and to ionizing radiation, such as a gamma-rays.

While steam-pressure sterilization can be effective, plastic packaging which will withstand the requisite temperature is more expensive than similar packaging which does not have to withstand the high-temperature. The penetration depth of high-energy electromagnetic radiation (e.g., gamma rays) is roughly six orders of magnitude greater than the size of the microorganism to be destroyed. Accordingly, high-energy radiation is effective for slow volume sterilization but inefficient for rapid surface sterilization. This inefficiency is manifested in long time scales for surface sterilization. Finally, while UV radiation has the right penetration depths for surface sterilization, sufficient intensities are difficult to achieve for providing the desired destruction rate.

SUMMARY OF THE INVENTION

Accordingly, it is an object of the invention to provide a more efficient sterilization process for food-product containers and the like. To that end, the method of the invention operates to cause a cold plasma to be disposed near a surface to be sterilized, and that cold plasma is then subjected to a pulsed voltage differential for producing energized ions in the plasma that are directed toward the surface. Those energized ions then operate to achieve spore destruction on a surface to be sterilized.

The cold plasma discharge with the parameters needed for the approach of the invention should be easily produced by a range of established techniques. The power requirements for the high voltage pulses are very modest.

A series of pulses of total duration in the range of one millisecond should be sufficient for the doses required. With pulses of this duration the charge buildup on insulating surfaces should be well within a usable range. If larger doses are required, additional pulsing can be used. The heating of the container surface is minimal for the doses required.

DETAILED DESCRIPTION

Figure 1:
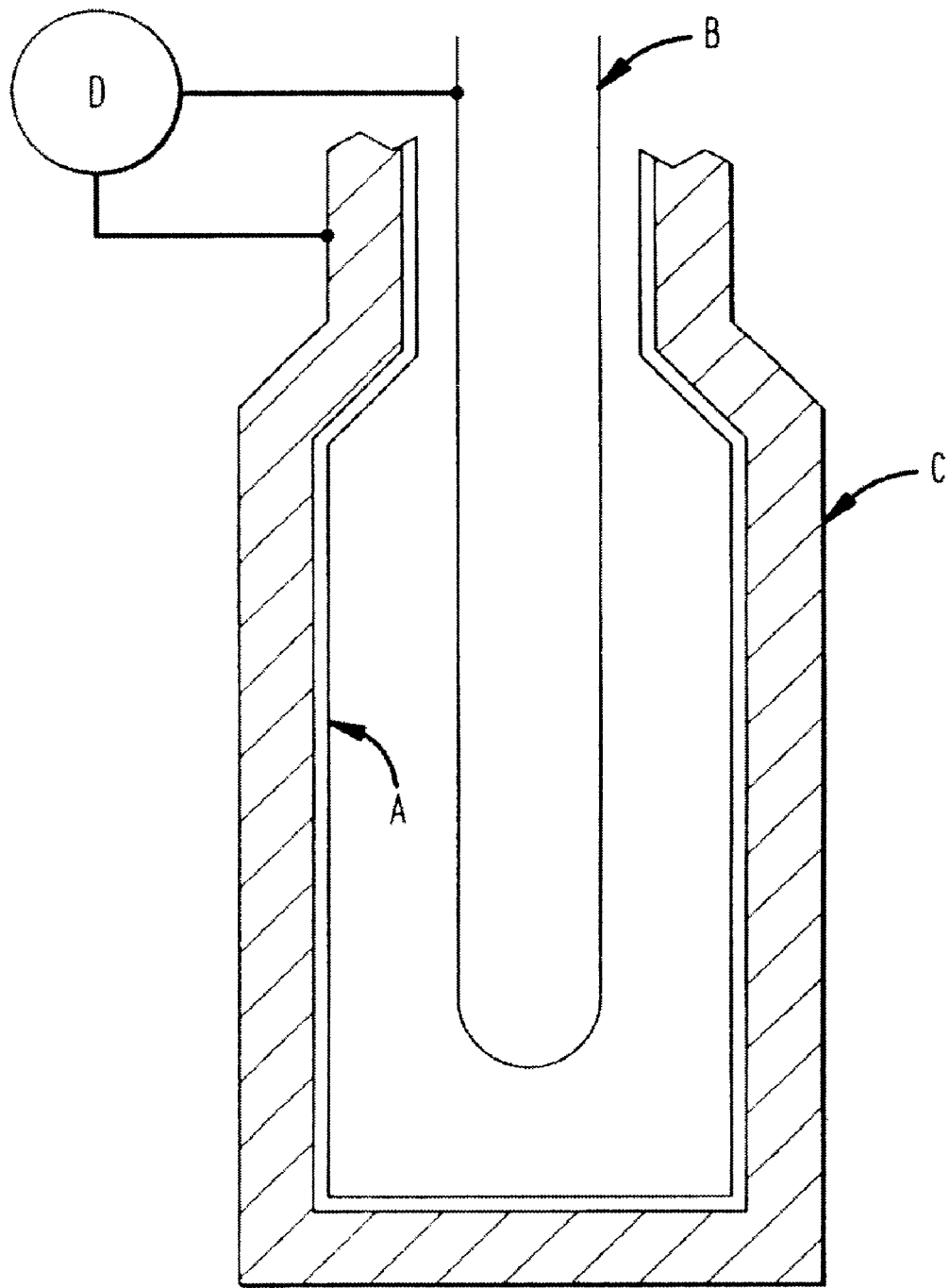
FIG. 1 provides a schematic depiction of the application of the method of the invention for a container to be sterilized.

An improved methodology is disclosed herein for sterilization of containers used for packaging contents requiring a sterile environment. In the preferred embodiment of the invention, the containers of interest are those used for packaging food products and the invention will be described in respect to such food-product containers. It should be understood, however, that the method of the invention is also applicable to the sterilization of containers for other products requiring sterile packaging, such as medical cosmetic and pharmaceutical products.

A primary object of sterilization for product packaging is, of course, the destruction of microorganisms that might otherwise contaminate the product so packaged. Among the more difficult microorganisms to eliminate during sterilization are bacterial spore. For the purpose of illustrating the operation and principle of the method of the invention, the focus of the description hereafter will be the destruction of such spore. However, the sterilization method of the invention is expected to be effective on the full range of microorganisms which may be encountered and all such applications are intended to be within the scope of the claimed invention.

Techniques for spore destruction can be divided into two categories: (1) techniques that destroy the spore shell to get to the spore center, and (2) techniques that directly impact the spore center. At their present state of development the former techniques take minutes or longer for spore destruction. This is too slow for production line applications. The latter techniques include heat and electromagnetic radiation. As explained in the Background section, both of these techniques suffer from significant limitations in respect to the sterilization of product packaging containers. The methodology of the invention overcomes the limitations of the prior art by directly impacting the spore center with high energy ions.

A. Description of the Preferred Embodiment

As a predicate to the description of the preferred embodiment, it is to be noted that light ions (e.g., hydrogen) having energies in the 20–70 keV or greater range have penetration depths comparable to spore sizes. This short range results in very high damage coefficients. Modest ion fluences (e.g. $3 \cdot 10^{-8}$ coul $cm^2$) in this energy range will provide damage in the Mrad range required for spore destruction. [The destruction of bacterial spores by energized ions is further explained by Russell, *The Destruction of Bacterial Spores*, Academic Press, 1982, p. 121.]

According to the method of the invention, a cold plasma is disposed near a surface to be sterilized and subjected to pulsed voltage differential with the surface that produces energized ions in the plasma directed toward the surface. Those energized ions then operate in a known manner to achieve spore destruction on the surface to be sterilized.

A range of approaches (e.g. rf or glow discharge) can be used to create low density (e.g. $10^8$ $cm^{-3}$) cold plasmas near the surface to be sterilized. The surface to be sterilized is then pulsed to the required voltage (e.g. 50 kV) for a series of short periods (e.g. 1–50 microseconds), and the resulting ion deposition will be in the range required. If the surface to be sterilized is a conductor, that surface may be constituted as one of the electrodes for the pulsed voltage potential across the plasma. If, on the other hand, the surface to be sterilized is an insulator (e.g. plastic) it can be backed by a conductor and the capacitive displacement current will support the charge densities required. In the event that a greater charge is required, the backing conductor can be pulsed with a greater number of pulse repetitions with a period between pulses to allow the low-density low-voltage plasma to discharge the insulator surface. Glow discharge cleaning with the cold plasma discharge could be used to help clean the surface of coatings over the microbes if desired.

FIG. 1 provides a schematic illustration of the application of the method of the invention to a generic container. The container (A) is evacuated to a desired pressure (illustratively, in the 0.1–100 milliTorr range). A gas feed is used to inject a working gas (e.g. hydrogen) into the container in this pressure range. A plasma discharge is initiated in the container with known techniques, such as glow discharge or rf. If a glow discharge is used, the electrode (B) could be segmented to act as an anode and cathode, or a low frequency voltage could be induced between the electrode and the conforming conductor (C) outside the container. If high frequency rf is used to initiate plasma discharge, the launcher could be any of a number of known configurations, including an external coil, the indicated electrodes or alternately driven segments of the external conductor. After the low density discharge has been initiated, a high voltage is driven between the internal electrode (B) and the conforming conductor (C) external to the container, by a power supply with modulator (D). Note that conforming conductor (C) may also be placed at or near the inside surface of the container, but in that case the conductor should be made porous in order to permit ions attracted thereto to pass through and reach the container surface. The polarity of the voltage will be established to attract ions to the container. The energetic ions will damage the microorganisms on the container surface.

In a further embodiment adapted for use with small containers having open mouths or where difficulty is experienced or expected in producing the low temperature discharge in a small space in the container, a more planer discharge could be generated above and into a group of containers and the ions accelerated into the container surfaces by the process described above.

B. Illustrative Operating Characteristics for Invention

For the purpose of illustrating the operation of the invention, it is assumed that one megaRad is required to assure spore destruction. It should be understood, however, that a somewhat higher dose may be required for some microorganisms. One Rad is one esu per cc of charge (i.e. $3.3\cdot10^{-10}$ $coul\cdot cm^{-3}\cdot Rad^{-1}$). Therefore $3.3\cdot10^{-10}$ $coul\cdot cm^{-3}\cdot Rad^{-1}\times1\cdot10^{6}$ $Rad=3.3\cdot10^{-4}$ $Coul\cdot cm^{-3}$ will be the required dose. If the penetration depth is one micron, then the surface charge will be $1\cdot10^{-4}$ $cm\times3.3\cdot10^{-4}$ $Coul\cdot cm^{-3}=3.3\cdot10^{-8}$ $Coul\cdot cm^{-2}$. If each high energy ion produces approximately 100 ion electron pairs, the surface charge required is in the $10^{-9}$ $Coul\cdot cm^{-2}$ range. For 50 keV ions the energy density will be only $1.65\cdot10^{-3}$ $joul\cdot cm^{-2}$.

It is noted that the penetration depth of energetic ions into microbes has some uncertainty because data is not available for microbes. However, data is available for materials that are sufficiently similar to support the validity of the process. The penetration depth in materials is strongly energy dependent and increases with increasing energy. The penetration depth decreases with increasing atomic number of the ions used. For this reason light ions, such as hydrogen, are preferable as a working gas. 50 keV hydrogen ions should be sufficient to penetrate about one micron for the analog material. In addition, it is believed likely that spore material is somewhat easier to penetrate.

As a test case, one can assume a cold plasma discharge with a hydrogen density of $1\cdot10^{8}$ $cm^{-3}$ and a temperature of 2 eV. The ion sound speed ($c_s$) will be about $1.4\cdot10^{6}$ cm/sec. The current density to an electrode will be about:

$$j=enc_s=1.6\cdot10^{-19}\ coul\times1\cdot10^{8}\ cm^{3}\times1.4\cdot10^{6}\ cm/sec=2\cdot10^{-5}\ A\cdot cm^{-2}$$

To achieve $3.3\cdot10^{-8}$ $Coul\cdot cm^{-2}$ will require a total pulse duration of about 1.5 msec.

The capacitance of a container surface with a thickness of approximately 0.5 mm and a dielectric constant of about 2 will be:

$$0.5\ \mu F\cdot m^{-2}$$

The voltage increase of the surface with a charge density of $3.3\cdot10^{-8}$ $Coul\cdot cm^{-2}$ will be about 700 volts. This voltage drop is small compared to the total voltage drop of approximately 50 kV as required. If increased charge densities are required, then more pulses can be used as outlined above.

Surface heating by the sterilization method of the invention is expected to be minimal. The solution to the heat diffusion equation for a step function heat deposition is an error function of the variable $x(Kt)^{-1/2}$, where (K) is the thermal diffusion coefficient. For simplicity, the penetration depth (h) is estimated as h $(Kt)^{1/2}$ for (K) approximately $4\cdot10^{-3}\cdot cm^{2}\cdot sec^{-1}$. The temperature increase can be estimated as T u/hC where u is the energy flux and C is the heat capacity of the surface. With u $1.5\cdot10^{-3}$ $J/cm^{2}$ and C 2 $J\cdot cm^{-3}\cdot K^{-1}$ the temperature increase for a 2-millisecond pulse is about ¼ centigrade. Thus, there is considerable temperature margin.

CONCLUSION

A novel method and apparatus for container sterilization has been described using energetic ions to penetrate and destroy microorganisms with a range of sizes. In particular these ions should be able to penetrate spore coatings for spore diameters up to and greater than a micron. For microorganisms without coatings these ions are expected to be effective in destroying sizes that are quite large. If conditions are encountered where the microorganisms are too large to be destroyed by energetic ions with a realizable energy, this method of the invention can be used in conjunction with other sterilization techniques.

Although the methodology of the invention, and illustrative applications of that methodology, have been described in detail, it should be understood that various changes, alterations and substitutions may be made therein without departing from the spirit and scope of the invention as defined by the appended claims.

What is claimed is:

1. A method for sterilization of container surfaces comprising the steps of:

evacuating said container to a desired pressure;

injecting a working gas into said container at said desired pressure;

causing a plasma discharge to be initiated in said working gas;

pulsing a voltage potential across said plasma discharge for a short period of time operative to produce energetic ions in said plasma; and accelerating said energetic ions toward said container surfaces using the pulsed voltage potential;

wherein said energetic ions effect a sterilization of said container by destruction of microorganisms on surfaces of said container.

2. The method of claim 1, wherein the short period of time comprises 1–50 microseconds.

3. The method for sterilization of claim 1, wherein said plasma discharge is initiated by a glow discharge technique.

4. The method for sterilization of claim 1, wherein said plasma discharge is initiated by an RF signal.

5. The method of sterilization of claim 1, wherein said energetic ions are deposited on said container surface by a capacitive displacement current.

6. The method for sterilization of claim 1, wherein said applied voltage is of a magnitude to impart an ion energy on the order of 50 keV.

7. A method for sterilization of interior surfaces of a container comprising the steps of:

forming a plasma discharge in a working gas disposed within said container;

pulsing a voltage potential between said plasma discharge and an interior surface of said container for a short period of time, said voltage potential being operative to produce energetic ions in said plasma; and accelerating said energetic ions toward the interior surfaces using the voltage potential;

wherein said energetic ions effect a sterilization of said container surfaces by destruction of microorganisms on said surface.

8. The method of claim 7, wherein the short period of time comprises 1–50 microseconds.

9. The method for sterilization of claim 7, wherein said plasma discharge is initiated by a glow discharge technique.

10. The method for sterilization of claim 7, wherein said plasma discharge is initiated by an RF signal.

11. The method for sterilization of claim 7, wherein said applied voltage is of a magnitude to impart an ion energy on the order of 50 keV.

12. An apparatus for sterilization of a container comprising:

means for evacuating said container to a desired pressure;

means for injecting a working gas into said container at said desired pressure;

a first electrode introduced through an aperture of said container and protruding into an interior portion thereof;

a second electrode established at a surface of said container; and a modulated power supply connected, between said first and said second electrode and operative to provide a pulsed voltage potential between said electrodes having a duration of 1–50 microseconds;

wherein a plasma discharge is caused to be initiated in said injected working gas and said pulsed voltage potential between said electrodes produces energetic ions in said plasma, said energetic ions being accelerated toward the surfaces of the container and effecting sterilization of said container by destruction of microorganisms on surfaces of said container.

13. The sterilization apparatus of claim 12, wherein a portion of said container structure is constituted as said second electrode.

14. The sterilization apparatus of claim 12, wherein said second electrode is disposed outside of said container and the energetic ions are deposited on the surface by a capacitive displacement current.

15. The sterilization apparatus of claim 12, wherein a polarization of said potential difference between said first and said second electrode is established to attract ions to an interior surface of said container.

16. The sterilization apparatus of claim 12, wherein said second electrode is constituted of a porous material and established proximate to interior surfaces of said container.

17. The sterilization apparatus of claim 12, wherein said potential difference between said first and said second electrode is established at a magnitude to impart an ion energy on the order of 50 keV.

* * * * *